US009044497B2

(12) United States Patent
Harel et al.

(10) Patent No.: US 9,044,497 B2
(45) Date of Patent: Jun. 2, 2015

(54) DELIVERY VEHICLE FOR PROBIOTIC BACTERIA COMPRISING A DRY MATRIX OF POLYSACCHARIDES, SACCHARIDES AND POLYOLS IN A GLASS FORM AND METHODS OF MAKING SAME

(75) Inventors: Mordechi Harel, Baltimore, MD (US); Keren Kohavi-Beck, Reshon Le-Zion (IL)

(73) Assignee: Advanced Bionutrition Corporation, Columbia, MD (US)

( * ) Notice: Subject to any disclaimer, the term of this patent is extended or adjusted under 35 U.S.C. 154(b) by 161 days.

(21) Appl. No.: 13/351,343

(22) Filed: Jan. 17, 2012

(65) Prior Publication Data

US 2012/0114621 A1    May 10, 2012

Related U.S. Application Data

(63) Continuation of application No. 12/159,407, filed as application No. PCT/US2006/049434 on Dec. 28, 2006, now Pat. No. 8,097,245.

(60) Provisional application No. 60/754,502, filed on Dec. 28, 2005.

(51) Int. Cl.
*A01N 63/00* (2006.01)
*A23L 1/00* (2006.01)
*A23L 1/0532* (2006.01)
*A23L 1/09* (2006.01)
*A23L 1/30* (2006.01)
*A61K 35/74* (2006.01)
*A61K 47/26* (2006.01)
*A61K 9/00* (2006.01)
*A61K 9/19* (2006.01)

(52) U.S. Cl.
CPC ............. *A61K 35/747* (2013.01); *A23L 1/0029* (2013.01); *A23L 1/0532* (2013.01); *A23L 1/09* (2013.01); *A23L 1/097* (2013.01); *A23L 1/3014* (2013.01); *A23V 2002/00* (2013.01); *A61K 9/0056* (2013.01); *A61K 9/19* (2013.01); *A61K 35/74* (2013.01); *A61K 35/742* (2013.01); *A61K 35/744* (2013.01); *A61K 35/745* (2013.01); *A61K 47/26* (2013.01)

(58) Field of Classification Search
CPC ................. A23V 2002/00; A23V 2250/5026; A23V 2250/64; A23V 2200/3204; A23V 2250/636; A23V 2200/224; A23L 1/0029; A23L 1/0532; A23L 1/09; A23L 1/097; A23L 1/3014; A61K 47/26; A61K 35/47; A61K 35/745; A61K 35/744; A61K 35/742; A61K 35/75; A61K 9/19
USPC ................... 435/177, 178, 260, 252.1, 252.2; 424/93.4, 93.46, 93.45, 93.44
See application file for complete search history.

(56) References Cited

U.S. PATENT DOCUMENTS

| | | |
|---|---|---|
| 3,241,977 A | 3/1966 | Mitchell |
| 3,897,307 A | 7/1975 | Porubcan |
| 4,337,242 A | 6/1982 | Markus |
| 4,656,767 A | 4/1987 | Tarrant |
| 5,227,373 A | 7/1993 | Alexander |
| 5,262,187 A | 11/1993 | Hahn |
| 5,407,957 A | 4/1995 | Kyle |
| 5,518,918 A | 5/1996 | Barclay |
| 5,637,494 A | 6/1997 | King |
| 5,658,767 A | 8/1997 | Kyle |
| 5,715,774 A | 2/1998 | Adey |
| 5,731,006 A | 3/1998 | Akiyama |
| 5,766,520 A | 6/1998 | Bronshtein |
| 5,908,622 A | 6/1999 | Barclay |
| 5,958,455 A | 9/1999 | Roser |
| 5,968,569 A | 10/1999 | Cavadini |
| 5,981,719 A | 11/1999 | Woiszwillo |
| 6,060,050 A | 5/2000 | Brown |
| 6,187,330 B1 | 2/2001 | Wang |
| 6,190,701 B1 | 2/2001 | Roser |
| 6,258,362 B1 | 7/2001 | Loudon |
| 6,267,958 B1 | 7/2001 | Andya |
| 6,290,991 B1 | 9/2001 | Roser |
| 6,306,345 B1 | 10/2001 | Bronshtein |
| 6,331,310 B1 | 12/2001 | Roser |
| 6,338,856 B1 | 1/2002 | Allen |
| 6,338,866 B1 | 1/2002 | Criggall |
| 6,451,567 B1 | 9/2002 | Barclay |
| 6,468,782 B1 | 10/2002 | Tunnacliffe et al. |

(Continued)

FOREIGN PATENT DOCUMENTS

| | | |
|---|---|---|
| CN | 101287449 | 10/2008 |
| EP | 0259739 | 3/1988 |

(Continued)

OTHER PUBLICATIONS

Bergogne et al. Molecular Crystals and Liquid Crystals (2000) 354: 79-89.*

(Continued)

*Primary Examiner* — Susan Hanley
(74) *Attorney, Agent, or Firm* — RatnerPrestia

(57) ABSTRACT

The disclosure relates to a solid glass matrix of polysaccharide, saccharides and polyols as delivery vehicles for preservation and post gastric administration of a probiotic. The delivery vehicle is capable of releasing the probiotic at their site of action. The present invention further includes methods of making and using the solid glass matrix delivery vehicle of the invention.

14 Claims, 8 Drawing Sheets

(56) References Cited

U.S. PATENT DOCUMENTS

| | | |
|---|---|---|
| 6,503,411 B1 | 1/2003 | Franks et al. |
| 6,509,146 B1 | 1/2003 | Bronshtein |
| 6,509,178 B1 | 1/2003 | Tanaka |
| 6,534,087 B2 | 3/2003 | Busson |
| 6,537,666 B1 | 3/2003 | Bronshtein |
| 6,565,871 B2 | 5/2003 | Roser et al. |
| 6,582,941 B1 | 6/2003 | Yokochi |
| 6,586,006 B2 | 7/2003 | Roser et al. |
| 6,589,560 B2 | 7/2003 | Foster et al. |
| 6,664,099 B1 | 12/2003 | Worrall |
| 6,716,460 B2 | 4/2004 | Abril |
| 6,726,934 B1 | 4/2004 | Prokop |
| 6,733,759 B2 | 5/2004 | Ivey |
| 6,790,453 B2 | 9/2004 | Porzio |
| 6,797,266 B2 | 9/2004 | Naidu |
| 6,811,792 B2 | 11/2004 | Roser et al. |
| 6,872,357 B1 | 3/2005 | Bronshtein |
| 6,884,866 B2 | 4/2005 | Bronshtein |
| 6,900,173 B2 | 5/2005 | Martin |
| 6,919,172 B2 | 7/2005 | DePablo |
| 6,964,771 B1 | 11/2005 | Roser |
| 7,005,280 B2 | 2/2006 | Barclay |
| 7,052,719 B2 | 5/2006 | Bernstein |
| 7,056,495 B2 | 6/2006 | Roser |
| 7,122,370 B2 | 10/2006 | Porubcan |
| 7,153,472 B1 | 12/2006 | Bronshtein |
| 7,258,873 B2 | 8/2007 | Truong-Le |
| 7,282,194 B2 | 10/2007 | Sung |
| 7,381,425 B1 | 6/2008 | Truong-Le |
| 7,396,548 B2 | 7/2008 | Kyle |
| 7,744,925 B2 | 6/2010 | Roser |
| 7,842,310 B2 | 11/2010 | Hwang |
| 7,927,858 B2 | 4/2011 | Mayeresse |
| 8,097,245 B2 * | 1/2012 | Harel et al. ........... 424/93.4 |
| 8,460,726 B2 | 6/2013 | Harel |
| 8,834,951 B2 | 9/2014 | Harel |
| 2001/0012610 A1 | 8/2001 | Bronshtein |
| 2001/0016220 A1 | 8/2001 | Jager |
| 2002/0192202 A1 | 12/2002 | Naidu |
| 2003/0017192 A1 | 1/2003 | Kanafani |
| 2003/0022333 A1 | 1/2003 | Bronshtein |
| 2003/0165472 A1 | 9/2003 | McGrath |
| 2004/0038825 A1 | 2/2004 | Leland |
| 2004/0047881 A1 | 3/2004 | Kyle |
| 2004/0081638 A1 | 4/2004 | Kyle |
| 2004/0175389 A1 | 9/2004 | Porubcan |
| 2004/0177392 A1 | 9/2004 | Barratt et al. |
| 2004/0219206 A1 | 11/2004 | Roser |
| 2004/0241313 A1 | 12/2004 | Nana |
| 2005/0019417 A1 | 1/2005 | Ko et al. |
| 2005/0032192 A1 | 2/2005 | Vesey |
| 2005/0079244 A1 | 4/2005 | Giffard |
| 2005/0100559 A1 | 5/2005 | Myatt et al. |
| 2005/0153018 A1 | 7/2005 | Ubbink |
| 2005/0241011 A1 | 10/2005 | Allnut et al. |
| 2005/0266069 A1 | 12/2005 | Simmons et al. |
| 2006/0008861 A1 | 1/2006 | Allnutt et al. |
| 2006/0024404 A1 | 2/2006 | Kyle |
| 2006/0120999 A1 | 6/2006 | Dhar et al. |
| 2006/0121468 A1 | 6/2006 | Allnutt |
| 2006/0127453 A1 | 6/2006 | Harel |
| 2006/0130162 A1 | 6/2006 | Kyle et al. |
| 2006/0147500 A1 | 7/2006 | Klingeberg |
| 2006/0222694 A1 | 10/2006 | Oh |
| 2006/0258623 A1 | 11/2006 | Harel |
| 2006/0265766 A1 | 11/2006 | Kyle |
| 2007/0020289 A1 | 1/2007 | Mattern |
| 2007/0031534 A1 | 2/2007 | Tsujimoto |
| 2007/0082008 A1 | 4/2007 | Harel et al. |
| 2007/0292952 A1 | 12/2007 | Dhar et al. |
| 2008/0044081 A1 | 2/2008 | Lieb |
| 2008/0044481 A1 | 2/2008 | Harel |
| 2008/0050497 A1 | 2/2008 | Mai |
| 2008/0102132 A2 | 5/2008 | Giner |
| 2008/0131514 A1 | 6/2008 | Truong-Le |
| 2008/0193546 A1 | 8/2008 | Roser |
| 2008/0194504 A1 | 8/2008 | Kyle |
| 2008/0229609 A1 | 9/2008 | Bronshtein |
| 2008/0241244 A1 | 10/2008 | Truong-Le |
| 2008/0261916 A1 | 10/2008 | Jaszberenyi |
| 2009/0155351 A1 | 6/2009 | Hejl |
| 2009/0162521 A1 | 6/2009 | Clinger |
| 2009/0181363 A1 | 7/2009 | Dhar |
| 2009/0203592 A1 | 8/2009 | Beermann |
| 2009/0208585 A1 | 8/2009 | Roser |
| 2009/0232894 A1 | 9/2009 | Chouvenc |
| 2009/0238890 A1 | 9/2009 | Piechocki |
| 2009/0246184 A1 | 10/2009 | Harel |
| 2009/0324636 A1 | 12/2009 | Piechocki |
| 2010/0015177 A1 | 1/2010 | Drew |
| 2010/0047393 A1 | 2/2010 | Glas |
| 2010/0074994 A1 | 3/2010 | Harel |
| 2010/0086638 A1 | 4/2010 | Kyle |
| 2010/0092521 A1 | 4/2010 | Dhar |
| 2010/0120014 A1 | 5/2010 | Bronshtein |
| 2010/0120676 A1 | 5/2010 | Boehm |
| 2010/0189767 A1 | 7/2010 | Shimoni et al. |
| 2010/0297231 A1 | 11/2010 | Vehring |
| 2011/0070334 A1 | 3/2011 | Rangavajla |
| 2012/0009248 A1 | 1/2012 | Truong-Le |
| 2012/0039956 A1 | 2/2012 | Harel |
| 2012/0040010 A1 | 2/2012 | Harel |
| 2012/0114621 A1 | 5/2012 | Harel |
| 2012/0135017 A1 | 5/2012 | Harel |
| 2012/0288483 A1 | 11/2012 | Harel |
| 2012/0322663 A1 | 12/2012 | Harel |
| 2013/0287896 A1 | 10/2013 | Harel |
| 2013/0296165 A1 | 11/2013 | Harel |

FOREIGN PATENT DOCUMENTS

| | | |
|---|---|---|
| EP | 0471904 | 2/1992 |
| EP | 11513700 | 11/1999 |
| EP | 1110462 | 6/2001 |
| EP | 1344458 | 9/2003 |
| GB | 1232057 | 5/1971 |
| GB | 2389787 | 12/2003 |
| JP | 05246856 | 9/1993 |
| JP | 06022746 | 2/1994 |
| JP | 11-506467 | 6/1999 |
| JP | 2001/505431 | 4/2001 |
| JP | 2004506437 | 3/2004 |
| JP | 2004525106 | 8/2004 |
| JP | 2004/528288 | 9/2004 |
| JP | 2005501268 | 1/2005 |
| JP | 2005519600 | 7/2005 |
| JP | 2005270100 | 10/2005 |
| JP | 2007522085 | 8/2007 |
| JP | 2009522280 | 6/2009 |
| JP | 2010512755 | 4/2010 |
| KR | 20050105669 | 11/2005 |
| KR | 1020050106559 | 11/2005 |
| WO | WO 96/40077 | 12/1996 |
| WO | 9824327 | 6/1998 |
| WO | WO 98/24882 | 6/1998 |
| WO | WO 01/12779 | 2/2001 |
| WO | 0136590 | 5/2001 |
| WO | 0215720 | 2/2002 |
| WO | WO 02/058735 | 8/2002 |
| WO | WO 02/061111 | 8/2002 |
| WO | WO 02/076391 | 10/2002 |
| WO | 03088755 | 10/2003 |
| WO | WO 03/089579 | 10/2003 |
| WO | WO 03/103692 | 12/2003 |
| WO | WO 2004/039417 | 5/2004 |
| WO | WO 2004/043139 | 5/2004 |
| WO | 2004080196 | 9/2004 |
| WO | 2004091307 | 10/2004 |
| WO | 2004112776 | 12/2004 |
| WO | WO 2004/112767 | 12/2004 |
| WO | 2005030299 | 4/2005 |
| WO | 2005060937 | 7/2005 |
| WO | WO 2005/084646 | 9/2005 |
| WO | WO 2005/105978 | 11/2005 |

(56) References Cited

FOREIGN PATENT DOCUMENTS

| | | |
|---|---|---|
| WO | WO 2005/117962 A1 | 12/2005 |
| WO | WO 2006/122299 | 11/2006 |
| WO | 2007035455 | 3/2007 |
| WO | 2007038926 | 4/2007 |
| WO | WO 2007/075988 | 5/2007 |
| WO | WO 2007/067207 | 6/2007 |
| WO | 2007079147 | 7/2007 |
| WO | 2007084059 | 7/2007 |
| WO | 2007084500 | 7/2007 |
| WO | 2007117511 | 10/2007 |
| WO | 2007136553 | 11/2007 |
| WO | 2008016214 | 2/2008 |
| WO | 2008056983 | 5/2008 |
| WO | 2008076975 | 6/2008 |
| WO | 2009002481 | 12/2008 |
| WO | 2009140327 | 11/2009 |
| WO | 2010002418 | 1/2010 |
| WO | 2010111347 | 9/2010 |
| WO | 2010118188 | 10/2010 |
| WO | 2010118205 | 10/2010 |
| WO | 2010138522 | 10/2010 |
| WO | 2010135495 | 11/2010 |
| WO | 2011094469 | 8/2011 |

OTHER PUBLICATIONS

De Giulio, B. et al. "Use of alginate and cryo-protective sugars to improve the viability of lactic acid and bacteria after freezing and freeze-drying." World Journal of Microbiology and Biotechnology, Kluwer Academic Publishers, DO, vol. 21, No. 5, Jul. 1, 2005, pp. 739-746.

Kerney, L. et al. "Enhancing the Viability of *Lactobacillus plantarum* inoculum by immobilizing the Cells in Calcium-Alginate Beads Incorporating Cryoprotectants." Applied and Environmental Microbiology, vol. 56, No. 10, Oct. 1990, pp. 3112-3116.

Selmer-Olsen, E. et al. "Survival of *Lactobacillus helveticus* entrapped in Ca-alginate in relation to water content, storage and rehydration." Journal of Industrial Microbiology & Biotechnology, vol. 23, 1999, pp. 79-85.

Chen, T., J. P. Acker, A. Eroglu, S. Cheley, H. Bayley, A. Fowler, and M. Toner. 2001. Beneficial effect of intracellular trehalose on the membrane integrity of dried mammalian cells. *Cryobiology* 43: 168-81.

Crowe, J. H., J. F. Carpenter, and L. M. Crowe. 1998. The role of vitrification in anhydrobiosis. *Annu Rev Physiol* 60: 73-103.

Crowe, L. M., and J. H. Crowe. 1992. Anhydrobiosis: a strategy for survival. *Adv Space Res* 12: 239-47.

Favaro-Trindade, C. S., and C. R. Grosso. 2002. Microencapsulation of *L. acidophilus* (La-05) and *B. lactis* (Bb-12) and evaluation of their survival at the pH values of the stomach and in bile. *J Microencapsul* 19: 485-94.

Isolauri E, Sutas Y, Kankaanpaa P, Arvilommi H, and S. S. 2001. Probiotics: effects on immunity. Review_*Am J Clin Nutr.* 73: 444S-450S.

Kailasapathy K, and C. J. 2000. Survival and therapeutic potential of probiotic organisms with reference to *Lactobacillus acidophilus* and *Bifidobacterium* spp. Review. *Immunol Cell Biol.* 78: 80-88.

Krallish I, Jeppsson H, Rapoport A, and H.-H. B. 1997. Effect of xylitol and trehalose on dry resistance of yeast. *Appl Microbiol Biotechnol.* 47: 447-51.

Liao, Y. H., M. B. Brown, A. Quader, and G. P. Martin. 2002. Protective mechanism of stabilizing excipients against dehydration in the freeze-drying of proteins. *Pharm Res* 19: 1854-61.

Linders Li, Wolkers WF, Hoekstra FA, and v. t. R. K. 1997. effect of added carbohydrates on membrane phase behavior and survival of dried *Lactobacillus plantarum. EClyobiology.* 35: 31-40.

Marteau PR, de Vrese M, Cellier CJ, and S. J. 2001. Protection from gastrointestinal diseases with the use of probiotics. Review. *Am J Clin Nutr.* 73: 430S-436S.

Perdigon G, Fuller R, and R. R. 2001. Lactic acid bacteria and their effect on the immune system. Review. *Curr Issues Intest Microbiol.* 2: 27-42.

Qiu L, Lacey MJ, and Bedding RA. 2000. Permeability of the infective juveniles of Steinernema carpocapsae to glycerol during osmotic dehydration and its effect on biochemical adaptation and energy metabolism. *Comp Biochem Physiol B Biochem Mol Biol.* 125: 411-9.

Shah, N. P. 2000. Probiotic bacteria: selective enumeration and survival in dairy foods. *J Dairy Sci* 83: 894-907.

Translation of Japanese Office Action for Japanese Patent Application No. 2008-548729, mailed Jul. 23, 2012.

Benedict, R.G. et al., "Preservation of Microorganisms by Freeze-Drying I. Cell Supernatant Naylor-Smith Solution, and Salts of Various Acids as Stabilizers for Serratia marcascens," Appl. Microbiol, 1958, vol. 6, No. 6, pp. 401-407.

European Office Action for Application No. 10 781 100.2-1403 dated Oct. 17, 2014.

Extended European Search Report for European Application No. 11817090.1-1358 dated Jun. 16, 2014.

International Search Report for International Application No. PCT/US2010/036098 mailed Feb. 14, 2011.

International Search Report for International Application No. PCT/US2011/022821 mailed Oct. 25, 2011.

Maltrin M100 Maltodrexin, 2006, XP055120984, Internet retrieves from the Internet: URL: http://www.tpipremixes.com/productpdfs/Maltodextrin.pdf, retrieved on Jun. 2, 2014.

Perry, Stephen F, "Freeze-Drying and Cryopreservation of Bacteria," Molecular Biotechnology, 1998, vol. 9, No. 1, pp. 59-64

Notice of Allowance mailed Jan. 15, 2015 in U.S. Appl. No. 13/911,636.

Office Acton mailed Jan. 14, 2015 in U.S. Appl. No, 13/321,708.

Russian Office Action mailed Dec. 18, 2014 in Application No. 2011151788/10(077759).

Notice of Allowance mailed Oct. 27, 2014 in U.S. Appl. No. 13/459,408.

Office Action mailed Oct. 27, 2014 in U.S. Appl. No. 13/208,459.

International Preliminary Report on Patentability and Written Opinion for PCT 4 International Application No. PCT/US2013/033505 issued Sep. 23, 2014.

Canadian Office Action mailed Oct. 10, 2014 in Canadian Application No. 2,785,815.

Abdelwahed et al., Advanced Drug Delivery Reviews, 58: 1688-1713 (2006).

Anal et al., "Recent advances in microencapsulation of probiotics for industrial applications and targeted delivery," Trends in Food Science and Technology, vol. 18, No. 5, Apr. 29, 2007, pp. 240-251.

Anderson, J.W., Johnstone, B.M. and Remley, D.T. (1999), Breastfeeding and cognitive development: a meta-analysis. Am J Clin Nutr, 70, 525-35.

Annear, D., "The preservation of leptospires by drying from the liquid state," Journal of General Microbiology, 27 (1962) 341-343.

Bazan, N.G. and Rodriguez de Turco E.B. (1994). Review: pharmacological manipulation of docosahexaenoic-phosphollpid biosynthesis in photoreceptor cells: implications in retinal degeneration. J. Ocul Pharmacol, 10, 591-604.

Bazab, N.G. and Scott, B.L. (1990), Dietary omega-3 fatty acids and accumulation of docosahexaenoic acid in rod photoreceptor cells of the retina and synapses. Ups J Med Sci Suppl, 48, 97-107.

Behrens, P. and Kyle, D. (1996). Microalgae as a source of fatty acids, J Food Sci, 3, 259-272.

Boswell KDB, Gladue R, Prima B, Kyle DJ (1992) SCO production of fementive microaldae. In: Kyle DJ, Ratledge C (eds) Industrial Applications of Single Cell Oils. American Oil Chemists Society, Champaign, IL., pp. 274-286.

Canadian Office Action mailed Apr. 6, 2011 in Canadian Application No. 2,673,120.

Capela, P., et al., "Effect of cryoprotectants, prebiotics and microencasulation on survival of probiotic organisms in yoghurt and freeze-dried yoghurt," Food Research International, 39 (2006) 203-211.

Chen et al., China Tropical Medicine, 7(4):654-55 (2007) (with partial English translation).

(56) References Cited

OTHER PUBLICATIONS

Chinese Search Report dated May 26, 2014 for application No. 201180039219.7 filed Aug. 12, 2011.
Crawford, M.A., Costeloe, K., Ghebremeskel, K. and Phylactors, A. (1998). The Inadequacy of the essential fatty acid content of present preterm feeds [published erratum appears In Eur J. Pediatr Feb. 1998; 157(2):160] . Eur J Pediatr, 157 Suppl 1. S23-7.
Crowe, J.H., Crowe., L.M., and Mouriadian, R., 1983, Cryobiology, 20, 346-356.
Desai et al., Pharmaceutical Research, 13(12):1838-45 (1996).
Esquisabel et al., 1997, J. Microencapsulation, 14, 627-638.
First Office Action with a Search Report issued by the State Intellectual Property Office of the People/s Republic of China on May 22, 2013 for Chinese Application No. 201180007562.3.
Grinstead G, Tokach M. Dritz, S, Goodband R, Nelssen J (2000) Effects of Spirulina platensis on growth performance of weanling pigs. Animal Feed Sci Technol 83:237-247.
He ML., Hollwich W, Rambeck WA (2000) Supplementation of algae to the diet of pigs: a new possibility to improve the iodine content in the meat. J Animal Physiol Animal Nutri 86:97-104.
Hincha, D., et al., "Protection of liposomes against fusion during drying by oligosaccharides is not predicted by the calorimetric glass transition temperatures of the dry sugars," European Biophysics Journal, 37 (2008) 503-508.
Hughes, V.X. and Hiller, S.L. (1990). "Microbiologic characteristics of Lactobacillus products used for colonization of the vagina."
Ikemoto, A., Kobayashi, T., Watanabe, S. and Okuyama, H. (1997). Membrane fatty acid modifications of PC12 cells by arachidonate or docosahexaenoate affect neurite outgroth but not norepinephrine release. Neurochem Res, 22, 671-8.
International Preliminary Report on Patetability for PCT International Application No. PCT/US2011/022821 dated Jul. 31, 2012.
International Search Report for International Application No. PCT/US2007/087771 mailed May 16, 2008.
Japanese Office Action issued in related Japanese Application No. 2013-524242, dated Jan. 21, 2014.
Japanese Office Action mailed Aug. 1, 2014 in Japanese Application No. 2012-513183, with translation.
Kets et al, "Citrate increase glass transition temperature of vitrified surose preparations," Cryobiology 48 (2004), 46-54.
Krasaekoopt et al. "Evaluation of encapsulation techniques of probiotics for yoghurt," International Dairy Journal, 2003, pp. 3-13.
M. Le Meste, et al., 2002, Glass Transition and Food Technology: A Critical Appraisal, Journal of Food Science, 67:2444-2458.
Martinez, M. (1990). Severe deficiency of docsahexaenoic acid in preoxisomal disorders: a defect of delta 4 desaturation. Neurology, 40, 1292-8.
Mazur et al., Hydration of Sodium Alginate in Aqueous Solution, Macromoecules, ACS Publications, Nov. 18, 2013, pp. 771-776.

Morgan, C., et al., "Preservation of micro-organisms by drying; a review," Journal of Microbiological Methods, 66 (2006) 183-193.
New Zealand Exmination Report dated May 18, 2012 in New Zealand Application No. 597053.
Niness, Inulin and Olgifructose: What are they?., J. Nutr, 129, 1999, pp. 1402S-1406S.
Office Action dated Mar. 21, 2014 in Russian patent application No. 2011151788/10(077759).
Office Action for Patent Application JP 2009-541634 mailed Jun. 25, 2012 (with English translation).
Office Action mailed Aug. 6, 2014 in Russian Application No. 2011151788/10 (077759).
Sanchez et al., 1999, Intl. J. Pharm. 185, 255-266.
Schwab, C., et al., "Influence of oligosaccharides on the viability and membrane properties of lactobacillus reuteri TMW1.106 during freeze-drying," Cryobiology, 55 (2007) 108-114.
Second Examination Report issued in Chilean Application No. 2011-001984, dated Jan. 24, 2014.
Second Office Action issued by the State Intellectual Property Office of the People/s Republic of China Feb. 8, 2014 in corresponding Chinese Application No. 2011800756.3, including a Search Report (with English translation).
Shin et al., Growth and Viability of Commerical Bifidobacterium spp in Skim Milk containing oligosaccharides and Inulin, Journal of Food Microbiology and Safety, 2000, vol. 65, No. 5, pp. 884-887.
Stordy, BJ. (1995). Benefit of docosahexaenoic acid supplements to dark adaptation in dyslexics. Lancet, 346 (8971): 385.
Substantive Examination Adverse Report mailed Aug. 29, 2014 in Malaysian Application No. PI 2011005733.
Sucrose, Sucrose structure, Webpage, Elmhurst College, 2003.
Supplementary European Search report in European Application No. EP 10781100.2-2405 dated Sep. 28, 2012.
Supplementary European Search Report for European Appln No. 11737688 dated Sep. 18, 2013.
Tobar et al., Oral Vaccination of Atlantic Salmon Salmo Salar against Salmon Rickettsial Septicaemia, presentation, World Aquaculture Society/s 2008 annual international conference (May 19-23, 2008).
Tobar et al., Oral Vaccination of Atlantic Salmon Salmo salar against Salmonid rickettsial septicaemia (SRS), abstract, World Aquaculture Society/s 2008 annual international conference (May 19-23, 2008).
Wong, Recent Patents on Drug Delivery & Formation 3:8-25 (2009).
Xu, L.Z., Sanchez, R., Sali, A. and Heintz, N. (1996).Ligand specificity of brain lipid-binding protein, J Biol chem, 271, 24711-9.
International Search Report for International Application No. PCT/US2006/49434 dated Sep. 26, 2007.
Zarate et al., ("Viability and biological properties of probiotic vaginal lactobacilli after lyophilization and refrigerated staorage into gelatin capsules," Process Biochemistry 41 (2006), 1779-1785.

* cited by examiner

DELIVERY VEHICLE FOR PROBIOTIC BACTERIA COMPRISING A DRY MATRIX OF POLYSACCHARIDES, SACCHARIDES AND POLYOLS IN A GLASS FORM AND METHODS OF MAKING SAME

CROSS-REFERENCE TO RELATED APPLICATION

The present application is a continuation application of U.S. patent application Ser. No. 12/159,407 filed on Nov. 21, 2008, now U.S. Pat. No. 8,097,245, which in turn claimed priority to PCT Application No. PCT/US2006/049434 filed in the U.S. Patent and Trademark Office, PCT Division, on Dec. 28, 2006, which in turn claimed priority to U.S. Provisional Patent Application No. 60/754,502 filed on Dec. 28, 2005, the contents of all applications are hereby incorporated by reference herein.

BACKGROUND OF THE DISCLOSURE

The disclosure relates generally to the field of a delivery vehicle for probiotic bacteria comprising a dry matrix of polysaccharides, saccharides and polyols in a glass form. Methods of making and uses thereof are also provided.

Probiotics are defined as live microbes that beneficially affect the host by modulating mucosal and systemic immunity, as well as improving intestinal function and microbial balance in the intestinal tract. Various nutritional and therapeutic effects have been ascribed to probiotics including: modulating immune response, lowering serum cholesterol concentrations, improving lactose intolerance symptoms, increasing resistance to infectious intestinal diseases, decreasing duration of diarrhea, reducing blood pressure, and helping to prevent colon cancer (Isolauri E et al. 2001, Kailasapathy K and J. 2000, Marteau P R et al. 2001, Perdigon G et al. 2001). In order to exert their beneficial effects on the host, probiotics must remain viable and reach the intestine in large numbers (Favaro-Trindade and Grosso 2002). However, maintaining long term stability of probiotics requires special storage conditions, since viability deteriorates rapidly over a short time period at ambient temperature and humid conditions (Shah 2000). In addition to poor shelf life, a significant loss of viability occurs upon exposure of the probiotics to gastric conditions of low pH and digestive enzymes. Existing preservation methods fail to provide satisfactory viability upon storage and gastric protection, especially if cells are stored at ambient or higher temperature and humidity.

Freeze-drying is often used for preservation and storage of bacteria because of the low temperature exposure during drying. However, it has the undesirable characteristics of significantly reducing viability as well as being time and energy-intensive. Freeze-drying involves placing the cells in solution, freezing the solution, and exposing the frozen solid to a vacuum under conditions wherein it remains solid and the water and any other volatile components are removed by sublimation. Standard freeze drying temperature of −30° C. to −70° C. are below the freezing point of water, but are well above the glass transition (Tg) temperature of the drying solution, which results in the undesirable effect of crystallization of water into ice. Freezing bacterial cultures results in substantial physical damage to the bacterial cell wall and subsequent loss of viability. Therefore, avoiding ice formation during cold storage of proteins, viruses, cells, tissues, and organs is an important problem in cryobiology.

The freezing point of water can be lowered by adding solutes that lower the vapor pressure of water. Freezing point depression is the physical basis on which essentially all currently used antifreeze agents (e.g., glycols, sugars and salts) perform. The disadvantage of freezing point depressors, known as cryoprotectants, is that large quantities of solutes (10% or more) are required to lower the freezing point by even a few degrees Celsius. At sufficiently high concentrations (typically 50% or more), conventional antifreeze agents can prevent ice formation, allowing aqueous solutions to be cooled to temperatures well below 0° C. without freezing. However, cryoprotectants are generally toxic at the high concentrations required to achieve glass formation or vitrification.

Other methods used to prepare dry and stable preparations of probiotics such as desiccation at ambient temperature and spray drying also has drawbacks. Desiccation at low or ambient temperature is slow, requires extra precautions to avoid contamination, and often yields unsatisfactory viability. Spray drying involves short excursions to relatively high processing temperatures and results in viability losses and limited storage times, even when stabilizing excipients are used (Lievense L C, van 't Riet K. 1994).

A viable and stable formulation for intestinal targeting of probiotics has been described by Simmonds et al. (2005). The process requires the granulation of lyophilized bacteria with microcrystalline cellulose stabilizers such as skim milk, salts or short chain sugars and a disintegrant such as starch or alginic acid. The granulated semi dry bacteria are then desiccated at 40-70° C. to reduce the residual moisture level to less than 2 percent. This is followed by coating with an enteric agent and plasticizer. This multi-step process results in large particle size (over 425 micron) and still results in up to 1.5 logs loss of viability. An additional disadvantage of this method is the high content of the enteric coating agents (over 25% of the microsphere weight), which are mostly synthetic and not recognized as food grade materials. An inherent disadvantage of a coating procedure is that the relative proportion of the coating to active agent goes up by a cubic function of the particle, as the particle size gets smaller, making the process less usable for the production of particles of sizes less than 300 micron.

An alternative method of bacterial preservation has been described which uses a foam formation technique while eliminating the formation of ice crystals (Bronshtein et al. 2004, Roser et al. 2004). This method requires high concentrations of sugars (a combination of methylated mono, di- and oligo-saccharides) in the drying media and a freeze drier that is equipped with a controlled vacuum system and temperature exposure, and the addition of foam forming elements and stabilizers. In spite of some advantages of this method in achieving longer shelf life stability, the foam-preserved bacteria are not protected from gastric excursion. Furthermore this process is difficult and costly to scale up because the foam requires, by definition, large volumes of space under reduced atmospheric pressure (i.e., in a vacuum) for the production of very little mass. In addition, this material is very sensitive to humidity and the product will take up water readily, decreasing the viability of the bacteria.

A composition containing a sugar (trehalose) partly in amorphous glassy phase and partly in crystalline hydrate phase has been proposed by Franks et al (2003). The crystalline hydrate phase serves as an agent to dehydrate the amorphous phase, thereby enhancing the glass transition temperature of the amorphous glassy state. This composition was shown to stabilize single molecules such as proteins or nucleotides. The glass transition temperature of a mixture depends, among other factors, on its chemical composition (sugars, proteins, salts) and the moisture content, with water acting as a plasticizer, depressing the glass temperature. If, at any time, the glass transition temperature (Tg) is exceeded, either by exposure to heat or in consequence of moisture migration into the product, the amorphous glassy state may become liable to irreversible phase separation by crystallization. If crystallization occurs, any residual amorphous phase will then be composed of the other components and the moisture, resulting in a further depression of the glass transition temperature.

A glass is an amorphous solid state that is obtained by controlled desiccation of a solution. The advantage of the glassy phase in achieving long term stability results from the fact that diffusion in glassy (vitrified) materials occurs at extremely low rates (e.g., microns/year). Glassy materials normally appear as homogeneous, transparent, brittle solids, which can be ground or milled into a powder. The optimal benefits of vitrification for long-term storage are observed under conditions where Tg is greater than the storage temperature. The Tg is directly dependent on water activity and temperature, and may be modified by selecting an appropriate combination of solutes (i.e., polysaccharides, sugars, salts and proteins).

Glass formation occurs naturally in some plant and arthropod species that are very desiccation tolerant. A number of mosses and ferns, so-called resurrection plants, can undergo severe desiccation and survive for many years in a quiescent metabolic state only to revive upon the return of water to the environment. In most cases, the adaptation characteristic is to increase internal concentrations of certain saccharides such as trehalose to a level that form glassy states.

Prior to the current disclosure, no one has been able to provide a common and cost effective solution to the separate problems facing the probiotic industry, namely maintaining long shelf life stability {i.e., viability) of bacterial cells at ambient temperatures and high water activities (or high humidity) and providing gastric protection to minimize losses of probiotic viability during the transit through the stomach. The present invention overcomes these problems.

BRIEF SUMMARY OF THE DISCLOSURE

The present invention encompasses compositions and methods of producing microparticles comprising a solid matrix in a glass form suitable for oral delivery. The compositions include a combination of a polysaccharide, a saccharide, a polyol and a probiotic bacteria. These compositions are designed to provide longer shelf life stability at ambient temperature in high water activity environments, and gastric protection of the probiotic. Furthermore, the method of production of this matrix involves processes that result in a minimal loss of probiotic viability.

Accordingly, one aspect of the invention comprises a preservation mixture of carbohydrates including at least one polysaccharide, one saccharide (mono di or oligo saccharide) and one polyol and at least one bacterium to be incorporated in the carbohydrate mixture.

In a preferred aspect, the bacteria in the preservation carbohydrate mixture are probiotic bacteria selected from, but not limited to the group consisting live *Lactobacillus, Bifidobacterium, Enterococcus, Propionobacterium, Bacillus*, and *Streptococcus*.

In another aspect of the invention the polysaccharide in the preservation mixture provides gastric protection and control release mechanism that gradually release the microbes at their site of action along the fore and hind gut of the animal or man. Examples of polysaccharides with gastric protection and a controlled release mechanism are hydrocolloid forming polysaccharides selected from the group including, but not limited to starch (including non-digestible starch), pectin, inulin, xanthan gum, alginate, alginic acid, chitosan, carrageenan, carboxymethyl cellulose, methyl cellulose, guar gum, gum arabic, locust bean gum and combinations thereof. Also preferably, the concentration of the polysaccharides in the preservation mixture is less than 10% w/v and more preferably less than 5% w/v of the preservation mixture.

In another aspect of the invention the saccharide/polyol combination in the preservation mixture is formulated so that it does not crystallize during drying and long-term storage at ambient temperature. A suitable glass formulation system includes, but is not limited to, trehalose/glycerol, trehalose/mannitol, trehalose/maltitol, trehalose/isomalt, trehalose/adonitol, trehalose/lactitol and trehalose/sorbitol. Trehalose is a naturally occurring, non-reducing disaccharide, which is associated with the prevention of desiccation damage in certain plants, microbes and animals that can dry out without damage and revive when rehydrated. Trehalose also has been shown to be useful in preventing denaturation of proteins, viruses and foodstuffs during desiccation (Chen et al. 2001, Crowe and Crowe 1992, Liao et al. 2002). Compared to sucrose, the glass transition temperature of trehalose is significantly higher (110° C. vs only 65° C.) (Crowe et al. 1998). However, trehalose alone is not always sufficient to stabilize bacteria especially at high temperature and humidity. In addition, cell membranes are more permeable to external sugar alcohols than to external trehalose (Krallish I et al. 1997, Linders L J et al. 1997, Qiu L et al. 2000). It is the synergetic effect of trehalose and sugar alcohols that provide better protection and improve cell viability over extended period of storage. Preferably, the concentration of the both saccharide and polyol in the mixture is less than 60% w/v and more preferably less than 40% w/v of the preservation mixture. The ratio between the saccharide and the polyol is preferably about 3:1 trehalose/polyol, although a ratio of 1:3 trehalose/polyol is also similarly effective in the preservation of certain probiotic species.

The present invention also provides methods of drying the mixture in glass form with a minimum loss of viability. It was discovered that vitrifying and efficient drying of the preservation mixture under vacuum was possible without the need of foam formation as described by Bronshtein (2004). Gelling or cross-linking the polysaccharides in the preservation mixture and slicing it to small pieces eliminated the need to foam the mixture in order to dry it under vacuum. It also reduced the formation of a rubbery product which happened often in the foaming process. Preferably, the preservation mixture, including the probiotic, is allowed to gel at low temperature and is then sliced and vacuum dried under conditions suitable for glass formation. More preferably the polysaccharide in the mixture is selected from the group of cross-linkable polysaccharides such as alginate, pectin or chitosan. The mixture is then extruded into $Ca^{++}$ bath and the strings or particles collected, rinsed with water, and then soaked in a suitable trehalose/polyol mixture followed by vacuum drying under conditions suitable for glass formation.

The present invention also provides methods of vacuum drying the preservation matrix without foaming or ice formation. The glass formation drying method comprises maintaining the matrix at 40° C., applying an initial vacuum of about 2,500 mTORR for a period of time followed by drying at less than 100 mTORR for another period of time. The initial product temperature is preferably maintained at or about 10-20° C. during the period at partially reduced pressure (2,500 mTORR) and then increased to 40-50° C., as the atmospheric pressure is decreased to less than 100 mTORR. A final drying step at 20° C. under maximum vacuum (ca. 10 mTORR) for additional period of time can also be of benefit for the final water removal. The dry matrix can then be ground or milled and, if necessary, sieved to a desired particulate powder.

DETAILED DESCRIPTION

Figure 1:
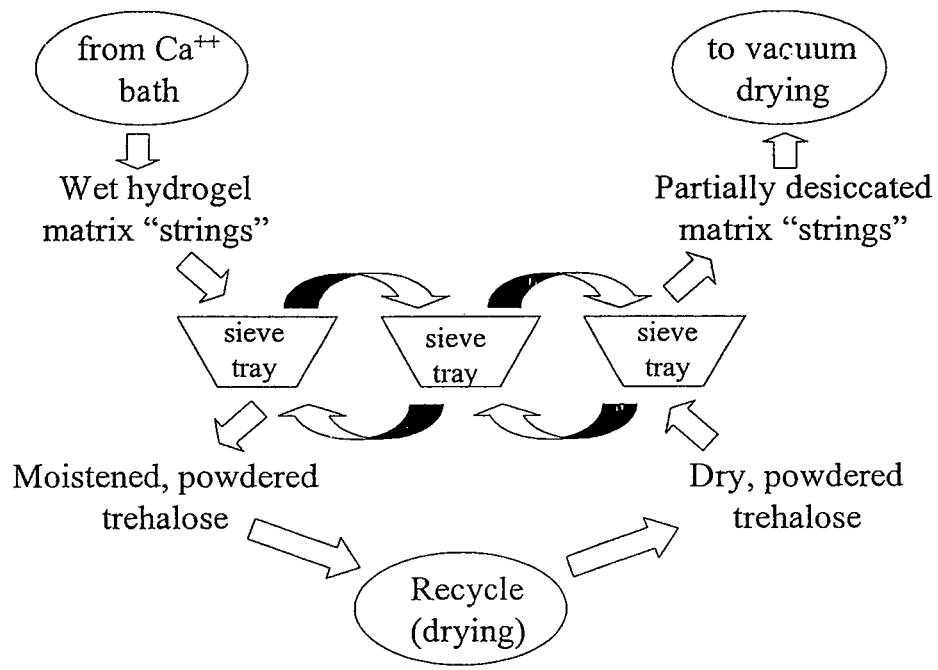
FIG. 1 is a flow diagram showing a method of countercurrent desiccation of a wet matrix hydro gel using a powdered saccharide (trehalose) as a stabilizing mixture.

The disclosure relates to a composition that is a solid glass matrix comprising a polysaccharide, saccharides, polyols and probiotic bacteria and methods for the efficient large scale production of this composition.

Definitions

As used herein, each of the following terms has the meaning associated with it in this section.

"Polysaccharides" refers to compounds consisting of a large number of monosaccharides linked with glycosidic bonds. As used herein, the term polysaccharides refers only to those containing more than ten monosaccharide residues.

"Saccharides" includes monosaccharides disaccharides and oligosaccharides.

"Polyols" refers in general to chemical compounds containing multiple hydroxyl groups. As used herein the term polyol means sugar alcohol, which is a hydrogenated form of carbohydrate, whose carbonyl group (aldehyde or ketone, reducing sugar) has been reduced to a primary or secondary hydroxyl group. Some common sugar alcohols are: mannitol, sorbitol, xylitol, isomalt, maltitol, lactitol "Vitrification" (i.e., glass formation) means formation of a glassy or noncrystalline amorphous material. As used herein the term glass or glassy state means a liquid phase of such high viscosity and low water content that all chemical reactions are slowed to a near standstill, and the bacteria cells become quiescent.

"Crystallization" refers to the formation of solid crystals from a homogeneous solution. It is essentially a solid-liquid separation.

"Cryoprotectant" refers to a chemical or compound that is used to prevent the formation of ice crystals during the supercooling of a water containing mixture.

Detailed Description

Fundamental to this invention is a polysaccharide capable of forming a strong gel matrix. This matrix preferably retains the bacteria and the preservation mixture even after being sliced into small pieces or formed into thin threads, strings, or particles. Additionally, the polysaccharide matrix preferably possesses a controlled release mechanism that protects the bacteria in the stomach, but is able to release the bacteria at their site of action along the intestine.

Several polysaccharides exhibit these requirements and are suitable for use as described herein. High amylose starch is a polysaccharide capable of forming firm gel after hydrating the starch granules in boiling water, dispersing the granules with the aid of high shear mixer and then cooling the solution to about 0-10° C. The firmness and strength of the gel depend on the concentration of the starch in the solution, with a maximal workable concentration of up to 10% w/v. The sliced starch gel matrix is also capable of retaining the live bacteria in the preservation mixture, and since it is mostly non-digestible by intestinal or gastric juices, the bacteria are protected from gastric destruction while within the starch matrix. The controlled release mechanism is provided by the fact that high amylose starch is readily digestible by the gut microflora at which time the delivered live bacteria are then released in their intact form.

Pectin is another suitable polysaccharide that performs very similar to high amylose starch. Pectin has an additional advantage since the strength of the pectin gel matrix can be further increased by the addition of divalent cations such as $Ca^{++}$ that forms bridges between carboxyl groups of the sugar polymers.

In a preferred embodiment of the present invention, alginate or a combination of alginate and non-digestible starch is used. Alginate can form a firm gel matrix by cross-linking with divalent cations. The alginate containing preservation solution can be hardened into a firm gel matrix by internally cross-linking the alginate polysaccharides with $Ca^{++}$ and then slicing the gel into small pieces while the bacteria and the preservation mixture are fully retained within the gel matrix. Another method of cross linking the solution containing alginate and preservation mixture is by extruding thin threads or strings of the solution into $Ca^{++}$ bath. The strings harden instantly upon interaction with $Ca^{++}$. The thin strings are harvested, rinsed with fresh water and then soaked again in the preservation solution but without the presence of polysaccharides. Another suitable method is to inject the thin threads into $Ca^{++}$ bath, which also contains a preservation mixture at equal concentration and proportion of that of the extruded solution. An alternative method of preparation of the matrix is to spray atomize the mixture into a bath containing $Ca^{++}$ cations. In such a procedure, small microparticles from 50 to 500 microns are produced. Such particles are harvested, rinsed and soaked in the preservation medium, or the bath itself may contain the preservation mixture as described above for the production of thin threads or strings.

The level of $Ca^{++}$ in the bath is constantly monitored and only sufficient amount of cations necessary to cross link the alginate are added at a time. This eliminates the need to rinse excessive $Ca^{++}$ from the strings or particles, thereby retaining all the sugar in the matrix, which would otherwise be washed away. In one preferred mode of the present invention, monitoring the $Ca^{++}$ cations within a range of 0.25-0.5% w/v in the cross-linking bath is sufficient to harden the extruded alginate solution without any damage to the probiotic bacteria. The gastric protection and controlled release trigger is also fulfilled by the use of alginate polysaccharide. A polymeric matrix containing alginate remains firm in the acidic environment of the stomach, thereby protecting the bacteria, but quickly disintegrates in the higher pH and phosphate-rich environment of the intestine. This results in the release of the probiotic bacteria at their site of action along the intestine.

The purpose of the preservation mixture is to provide protection from temperature and moisture excursions of the final product without undue loss of viability of the probiotic bacteria. An ideal mixture contains a combination of saccharides and sugar alcohols that form an amorphous glassy phase with a glass transition temperature (Tg) well above ambient temperature and water activity of the product. Trehalose alone is not always sufficient to stabilize bacteria, especially at high temperature and humidity. A more suitable mixture was found to be a combination of trehalose and additional sugar alcohol that provides a synergetic effect of better protection and improved cell viability over extended periods of storage. In addition to sugar alcohols and other long chain polyalcohols, other preservation agents include sucrose, lacto sucrose, raffinose, maltodextrose, sepharose and dextran. These compounds may synergistically improve the preservation of certain bacteria species.

The concentration and proportion of different carbohydrates in the preservation mixture depends on several factors, but most particularly on the bacteria species, strain, and drying conditions. The present invention discloses several optimal concentrations and sugar proportions suitable for inclusion in the preservation mixture for a number of probiotic bacteria. Preferably, the carbohydrate concentration should be less than about 50%, as higher concentrations may interfere with effective drying.

The preservation mixture optionally include other additives that contribute to the overall stability of the probiotic bacteria. Suitable additives include proteins, amino acids, diluents, chelating agents, buffers, preservatives, stabilizers, antioxidants, and lubricants. Specific examples of such additives would include, but are not limited to: amino acids, lysine, glycine, L leucine, isoleucine, arginine, cysteine; proteins, human serum proteins, egg albumin, gelatin; buffers, various sodium phosphate buffers, citric/citrate buffers; preservatives, derivatives of hydroxybenzoic acids; antioxidants, vitamin E, ascorbic acid; lubricants, water miscible silicone/silicates; chelating agents, citric acid, EDTA, EGTA.

In a preferred mode of the present invention, the sliced gel or thin threads or strings are dried in such a way that a glass is formed. Several drying methods can be employed, including, but not limited to, air drying at ambient temperature, spray drying, fluidized bed drying, vacuum drying, and freeze drying. As used herein, the glass containing the dried bacteria cells preferably contains a residual moisture content of less than about 5%, and, more preferably, less than about 2%.

Drying is preferably performed under vacuum in a freeze drier at a product temperature above the freezing temperature of water under such conditions. In general, vacuum drying are performed in two stages. The first stage involves moderately reduced pressure (ca. 2500 mTOR) at mild temperatures (20° C.), while the second stage involves lower pressures (i.e., higher vacuum –100 mTOR) at higher temperature (up to about 50° C.). This process can be achieved using a programmable control system for vacuum pressure and product temperature. The vacuum and temperature conditions for the first drying stage are adjusted empirically according the size of the drier, heat transfer capacity, and the product load, but the goal is to keep the product above its freezing temperature while maximizing the water evaporation rate. In one embodiment, the temperature is initially maintained at about 20° C. for about 16 hours, followed by gradually increasing the temperature to about 50° C. for the following 48 hours. These drying conditions allow the formation of glassy state wherein the bacteria are locked in a quiescent state inside the polysaccharide matrix.

In a preferred embodiment, the probiotic bacteria are dried as follows: the initial vacuum pressure is adjusted to about 2500 mTOR, with initial shelf temperature of 40° C. for 12 hours, followed by incrementally reducing the atmospheric pressure (i.e., increasing the vacuum) to less than 100 mTOR at a rate of 125 mTOR/hr. Once the vacuum reaches 100 mTOR, the sample is maintained at 40° C. for an additional 12 hours. Following this protocol, the drying procedure is completed within 48 hours without substantially compromising viability. In accordance with the present invention, the large surface area of the sliced and chopped gel or strings greatly increases evaporation rate without the need to boil or foam the product, thus eliminating inconsistent drying conditions and splattering of the foaming product solution in the vacuum chamber. Additionally, the disclosed composition and method of drying results in a higher loading capacity of product as compared to the foam drying method, that permits only a thin layer of solution to foam and dry efficiently.

An alternative drying procedure for the freshly prepared matrix strings or particles includes a controlled desiccation of the matrix by addition of the hydrogel to a certain volume (preferably 1:10 by weight) of dry powdered saccharide such as trehalose or dry powdered preservation mixture. During this process, the hydrogel is rapidly desiccated at ambient temperature, concentrating the preservation material in the matrix itself. The process is preferably set up in a countercurrent fashion where the fully hydrated hydrogel matrix containing the bacteria is added to one end of the process stream and fresh, dry powdered preservation saccharide flows from the opposite direction (FIG. 1). The wetted powdered saccharide material are dried at elevated temperature and reused while the partially desiccated hydrogel then goes on to the second stage of vacuum drying described above. This process significantly reduces the drying time and process costs.

The resultant matrix-bound glass material containing the dried, stabilized probiotic bacteria has a Tg sufficiently high to preserve the bacteria at ambient temperature (up to 30° C.) in a relative humidity of 33%. Generally, the higher the Tg, the higher the allowable storage temperature and humidity. Tg of the dry glassy preservation mixture of the present invention is determined using standard techniques in the art, such as differential scanning calorimetry.

The methods and compositions of the invention facilitate the development of several products, including, but not limited to: live bacterial vaccines in a dry stable form, live bacterial nutraceuticals (probiotics) in a dry stable form, live bacterial starter cultures in a dry stable form, live bacteria in a dry stable form for agricultural, aquaculture, or bioremedial use, and live bacterial cultures in a dry stable form for the biotechnology industry.

The following examples illustrate various aspects of the present invention, relating to producing a delivery vehicle comprising a dry and stable matrix of polysaccharides, saccharides, polyols and probiotic bacteria in a glass form. The compositions and drying methods are adapted to stabilize and preserve several probiotic bacteria in storage and gastric environment.

EXAMPLES

The subject matter of this disclosure is now described with reference to the following Examples. These Examples are provided for the purpose of illustration only, and the subject matter is not limited to these Examples, but rather encompasses all variations which are evident as a result of the teaching provided herein.

Example 1

High amylose starch (100 g Novation, National Starch and Chemical, Bridgewater, N.J.) was mixed with 150 ml of water at ambient temperature. The starch mixture was then slowly added to 850 ml of boiling water under vigorous mixing using a standard household blender. Once complete dispersion of the starch granules was observed (using a binocular microscope), the starch solution was allowed to cool and 300 g of trehalose and 100 g isomalt (both from Cargill Minneapolis, Minn.) were then dissolved in the mixture. Sodium alginate (15 g) was added to the slurry and the entire mixture was allowed to cool to room temperature. *Lactobacillus paracasei* (200 g frozen paste direct from fermentation harvest) was then mixed well into the slurry and the slurry was extruded into a 1000 ml bath (held at 0-5° C.) containing 5 g $CaCl_2$, 300 g trehalose and 100 g isomalt using a syringe equipped with 18 G needle. The $CaCl_2$ bath was gently stirred while injecting the slurry. The matrix strings were allowed to cross-link for 30 minutes and were then harvested and blotted on paper towel. The composition of the gel matrix is provided in Table 1.

TABLE 1

| Gel matrix composition (g dry weight/100 g) | |
| --- | --- |
| High amylose (70% amylose) | 10 g |
| trehalose | 30 g |
| Isomalt | 10 g |
| Sodium Alginate | 1.5 g |
| *L. paracasei* | 20 g |
| Water | 100 g |

The thin threads were loaded on a tray (13×10 inch) and placed in a freeze drier (Virtis Advantage, Virtis, Gardiner, N.Y.). The condenser was set to −70° C. and shelf temperature was set to 40° C. When the product had warmed up to the shelf temperature (measured by a pair of temperature sensors plugged in the wet material), the vacuum was initiated and controlled at about 2500 mTOR with an external vacuum controller (Thyr-Cont, Electronic, GmbH). As the atmospheric pressure decreased, the product temperature fell to and stabilized at about −2° C. After 12 hours, the product temperature had increased to about 10° C. At this point, the atmospheric pressure was dropped by about 500 mTOR every 4 hours until full vacuum pressure of 10 mTOR was established. Over this time period of increasing vacuum, the product temperature was carefully maintained at or above −5° C. Twelve hours after establishing full vacuum, the dried product was taken out of the freeze drier and ground to fine powder using standard coffee grinder.

Example 2

100 g of trehalose and 300 g isomalt (both from Cargill Minneapolis, Minn.) were added to 1000 ml water and allowed to dissolve. Sodium alginate (15 g) was mixed into the slurry and allowed to cool down to room temperature. *Lactobacillus paracasei* (200 g frozen paste as in Example 1) was then added to the slurry, followed by 5 g of calcium phosphate dibasic and 5 g of gluconolactone. The slurry was allowed to cross-link at room temperature over the next 4 hours. The firm gel was sliced to thin and long threads through cheese grinder and blotted on paper towel. The composition of the gel matrix is provided in Table 2.

TABLE 2

| Gel matrix composition (g dry weight/100 g) | |
| --- | --- |
| trehalose | 10 g |
| Isomalt | 30 g |
| Sodium Alginate | 1.5 g |
| *L. paracasei* | 20 g |
| Water | 100 g |

The thin threads were loaded on a tray (13×10 inch) and placed in a freeze drier for drying as outlined in example 1.

Example 3

300 g of trehalose (Cargill Minneapolis, Minn.) and 100 g mannitol (Sigma) were added to 1000 ml water and allowed to dissolve. Sodium alginate (15 g) and pectin (5 g) were mixed into the slurry and the slurry was allowed to cool down to room temperature. *Lactobacillus acidophilus* (200 g frozen paste, directly from a fermentation harvest) was mixed well into the slurry. The slurry was then extruded through a syringe equipped with 18 G needle into 1000 ml bath (0-5° C.) containing 5 g $CaCl_2$, 300 g trehalose and 100 g mannitol. The $CaCl_2$ bath was stirred while extruding the slurry. The formed strings were allowed to cross-link for 30 minutes, harvested, and blotted on paper towel. The composition of the gel matrix is provided in Table 3.

TABLE 3

| Gel matrix composition (g dry weight/100 g) | |
| --- | --- |
| trehalose | 30 g |
| Mannitol | 10 g |
| Sodium Alginate | 1.5 g |
| Pectin | 0.5 g |
| *L. acidophilus* | 20 g |
| Water | 100 g |

The thin threads were loaded on a tray (13×10 inch) and placed in a freeze drier for drying as outlined in example 1.

Example 4

Optimizing Trehalose Concentration in the Preservation Media

Figure 2:
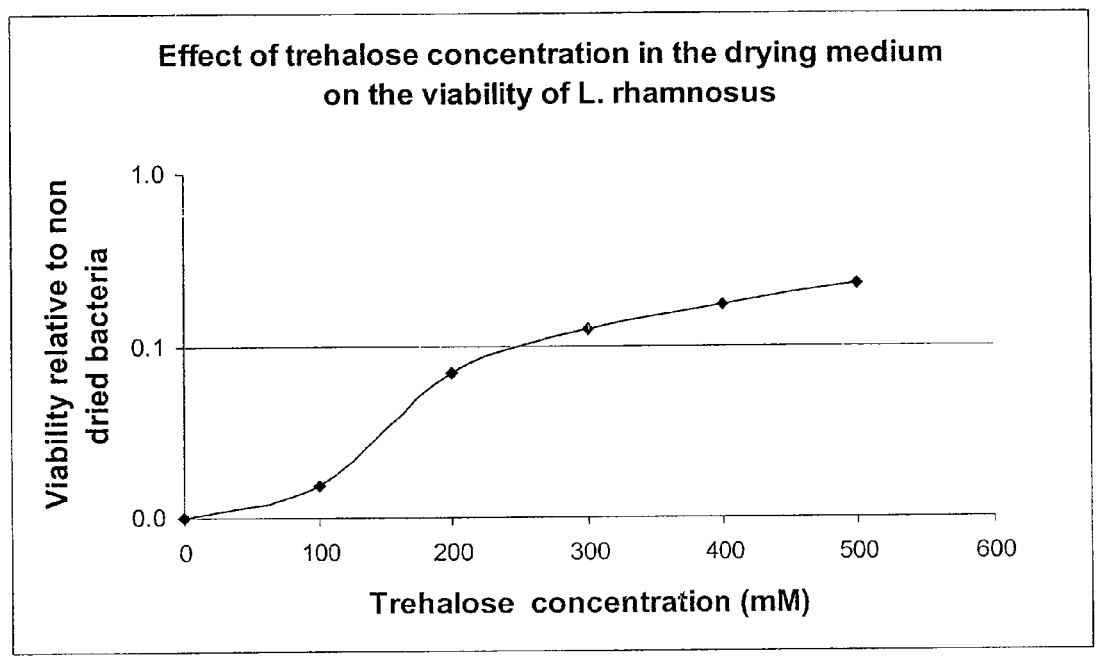
FIG. 2 is a graph that depicts the effect of trehalose concentration in the drying medium on bacteria viability. Maximal viability *L. rhamnosus* was achieved at 0.5 M trehalose concentration. *L. rhamnosus* was air-dried for 3 days in a laminar flow hood in the presence of increasing concentration trehalose.

Dry powdered *L. rhamnosus* (LCS-742, Morinaga Milk Industry Co., LTD., Kanagawa, Japan) was added to various concentrations of trehalose in bacterial culture media (L.MRS) and allowed to desiccate in a laminar flow hood at ambient temperature for 3 days. Bacteria viability as a function of trehalose concentration was measured at the end of the 3-day drying period. Dry bacterial powder or desiccated samples were reconstituted in sterile 50 mM PBS buffer pH 7.4. After homogenizing, solutions of reconstituted cultures were diluted (by 10-fold increments) in PBS buffer and plated in triplicate on L.MRS agar. After incubation at 35° C. for 48-72 hours, the number of colony forming units (CFU) was determined and *L. rhamnosus* viability was found to be highest at an initial trehalose concentration of 0.5 M (FIG. 2).

Example 5

The Effect of Different Sugar Alcohols on Drying Preservation of *L. paracasei*

Figure 3:
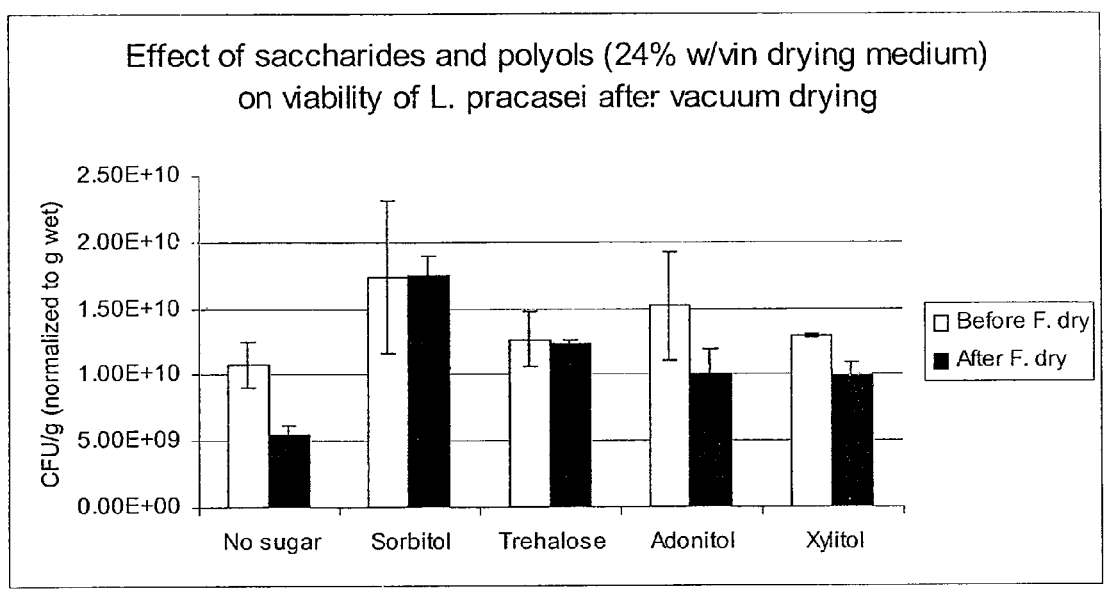
FIG. 3 is a bar graph that depicts the effect of saccharides and polyols (at total concentration of 24% w/v in drying medium) on the after drying viability of *L. pracasei*.

*L. paracasei* was prepared and dried as described in example 2 except that total sugar concentration was 24% and starch concentration was 2% in the preservation media. Several sugar alcohols were tested for their effect on the bacteria viability after drying. FIG. 3 shows that trehalose and sorbitol provided the best protection for the bacteria using this drying and preservation process.

Example 6

The Effect of Different Sugar Proportions on Drying Preservation of *L. acidophilus*

Figure 4:
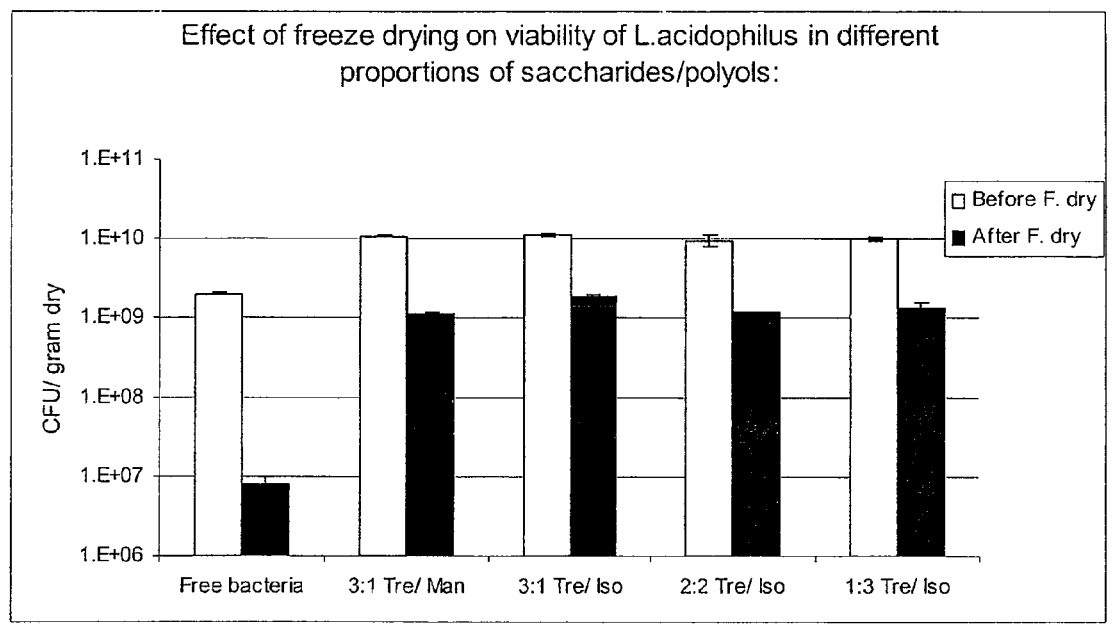
FIG. 4 is a bar graph that depicts the effect of different proportions of saccharides/polyols (trehalose/mannitol or trehalose/isomalt) in a mixture of polysaccharides (2% starch, 1% sodium alginate and 0.5% pectin) on viability of *L. acidophilus* after vacuum drying (the total concentration of the saccharides and polyols is 30% w/v).

*L. acidophilus* was dried as described in example 3 except that different proportions of trehalose/mannitol or trehalose/isomalt were used and the final mixture contained a combination of 3 polysaccharides (2% starch, 1% sodium alginate and 0.5% pectin). The viability of *L. acidophilus* after vacuum drying is shown in FIG. 4. In all cases, the preserved bacteria had a far greater viability compared with bacteria dried without the saccharide/polyol mixtures, and the different ratios of saccharide to polyol used in the preservations mixtures yielded similar protection capabilities for *L. acidophilus*.

Example 7

Stability of *L. acidophilus* in 45° C. at 0% or 33% Relative Humidity.

Figure 5:
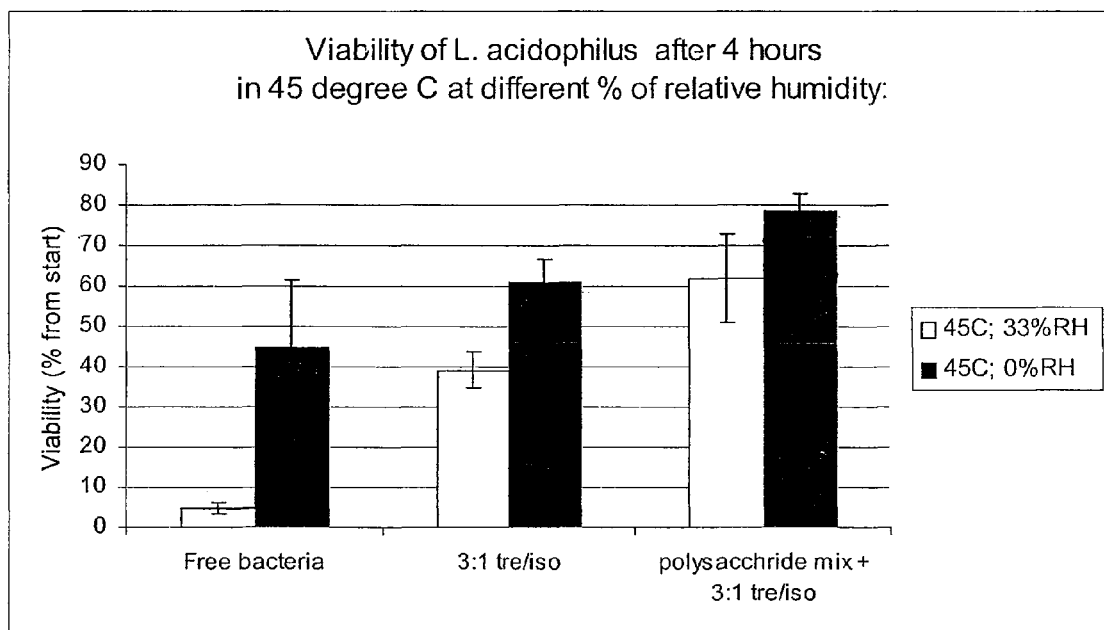
FIG. 5 is a bar graph that depicts the effect of polysaccharide mix (2% starch, 1% sodium alginate and 0.5% pectin) with 3:1 trehalose/isomalt (the total concentration of the saccharides/polyols is 40% w/v) on viability of dry *L. acidophilus* in 45° C. at 0% or 33% relative humidity.

*L. acidophilus* was dried as described in example 6. The dried bacteria was placed in temperature and humidity control incubator set at 45° C. and 0% relative humidity, or 45° C. and 33% relative humidity for 4 hours. Viability of the bacteria was measured before and after the temperature and humidity exposure. FIG. 5 shows that the polysaccharide mixture (2% starch, 1% sodium alginate and 0.5% pectin) provided additional protection to that of trehalose/isomalt alone or free bacteria.

Example 8

Stability of the Composition of the Present Invention in Simulated Gastric Juices

Figure 6:
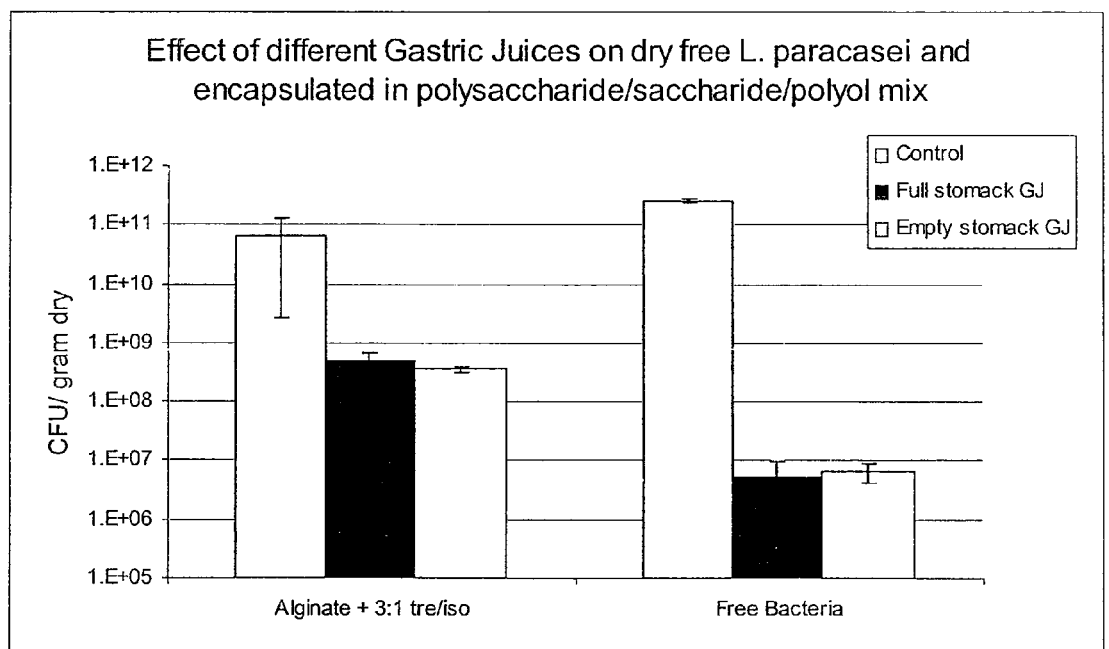
FIG. 6 is a bar graph that depicts the effect of full stomach (12% non fat skim milk, 2% glucose, 1% yeast extract and 0.05% cysteine; pH 2) or empty stomach (0.32% pepsin, 0.2% sodium chloride, pH 1.2) simulated gastric juices on *L. paracasei* dried in free form or in glass form of polysaccharide/saccharide/polyol mix.
Figure 7:
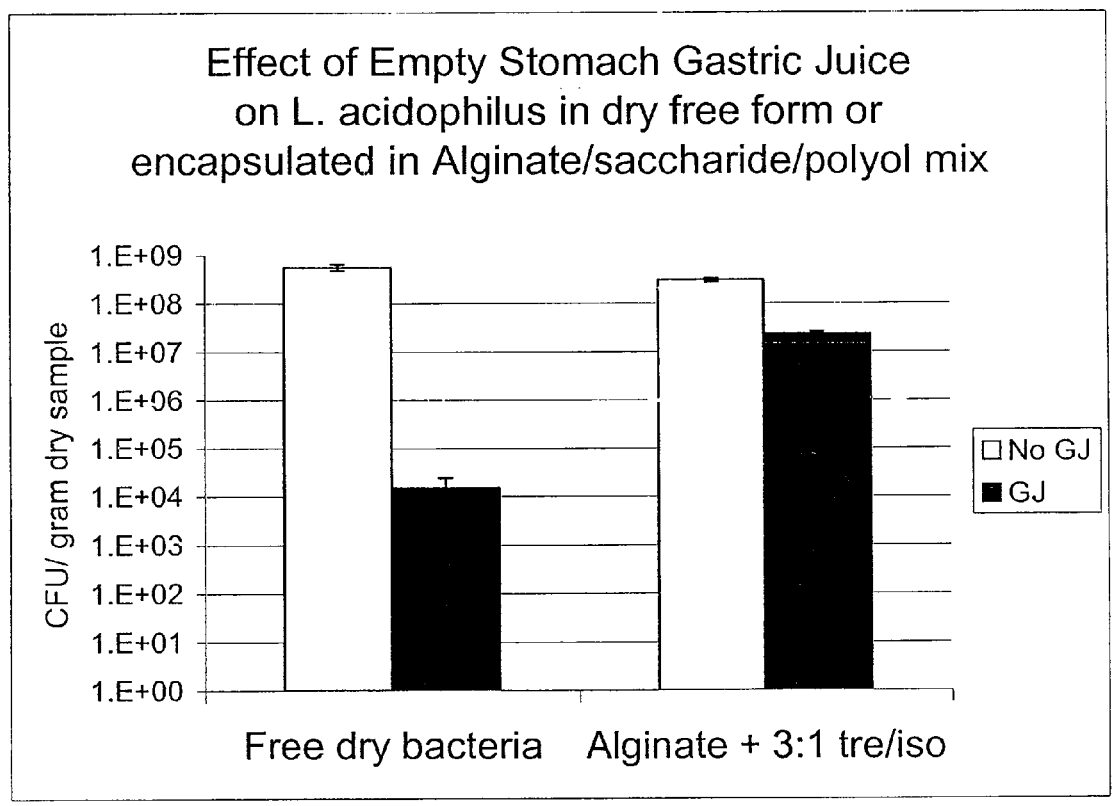
FIG. 7 is a bar graph that depicts the effect of empty stomach (0.32% pepsin, 0.2% sodium chloride, pH 1.2) simulated gastric juice on *L. acidophilus* dried in free form or in glass form of polysaccharide/saccharide/polyol mix.

*L. acidophilus* and *L. paracasei* were prepared and dried as described in example 2. The dry powder matrix-glass bacteria was then exposed for 2 hours to simulated gastric juice (full stomach –12% non fat skim milk, 2% glucose, 1% yeast extract and 0.05% cysteine; pH 2; or empty stomach –0.32% pepsin, 0.2% sodium chloride, pH 1.2). Bacterial viabilities were recorded before and after the exposure to the simulated gastric juices. FIGS. 6 and 7 demonstrate a significant protection of the bacteria in the drying composition of the instant invention in the different gastric conditions.

Example 9

300 g of trehalose (Cargill Minneapolis, Minn.) and 100 g egg albumen (Sigma) were added to 1000 ml water and allowed to dissolve. Sodium alginate (15 g) and pectin (5 g) were mixed into the slurry and the slurry was allowed to cool down to room temperature. *Lactobacillus* GG (200 g frozen paste direct from fermentation harvest) was then added to the slurry, followed by 5 g of calcium phosphate dibasic and 5 g of gluconplactone. The slurry was allowed to cross-link at room temperature over the next 4 hours. The firm gel was sliced to thin and long threads through cheese grinder and blotted on paper towel. The composition of the gel matrix is provided in Table 4.

TABLE 4

| Gel matrix composition (g dry weight/100 g) | |
|---|---|
| trehalose | 30 g |
| egg albumen | 10 g |
| Sodium Alginate | 1.5 g |
| Pectin | 0.5 g |
| *Lactobacillus* GG | 20 g |
| Water | 100 g |

The thin threads were loaded on a tray (13×10 inch) and placed in a freeze drier for drying as outlined in example 1.

Example 10

Stability of the Composition of the Present Invention in 40° C. and 15% or 33% Relative Humidity.

Figure 8A:
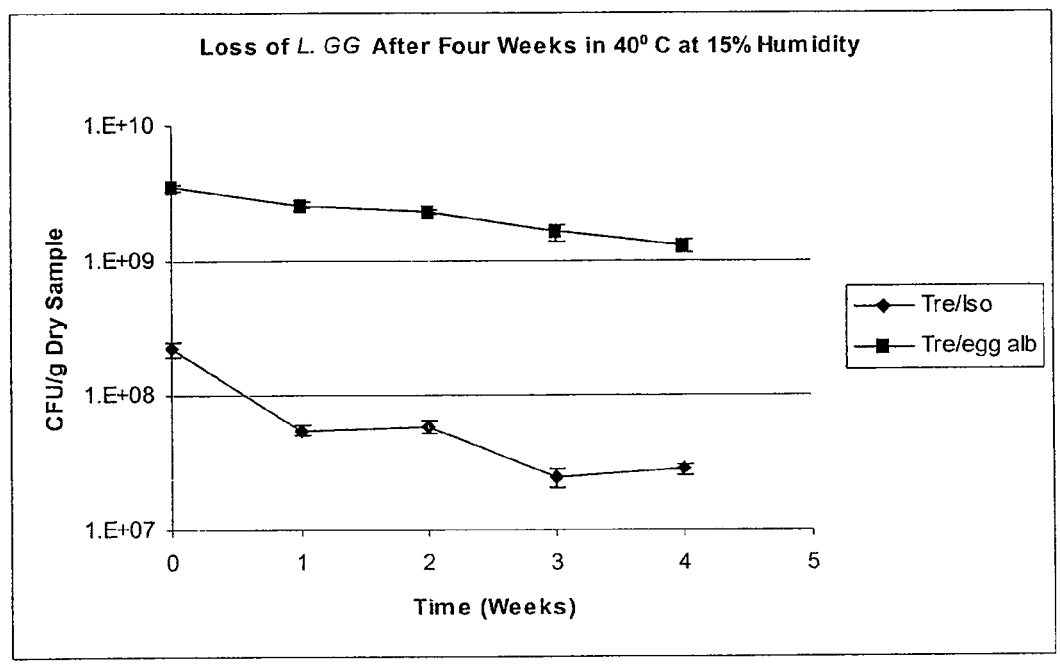
FIGS. 8A and 8B depict the effects of carbohydrate/ polysaccharide/egg albumen mix (trehalose/alginate/pectin/ egg albumen 30:1.5:0.5:10) on viability of dry *Lactobacillus* GG in 40° C. at (A) 15% or (B) 33% relative humidity.
Figure 8B:
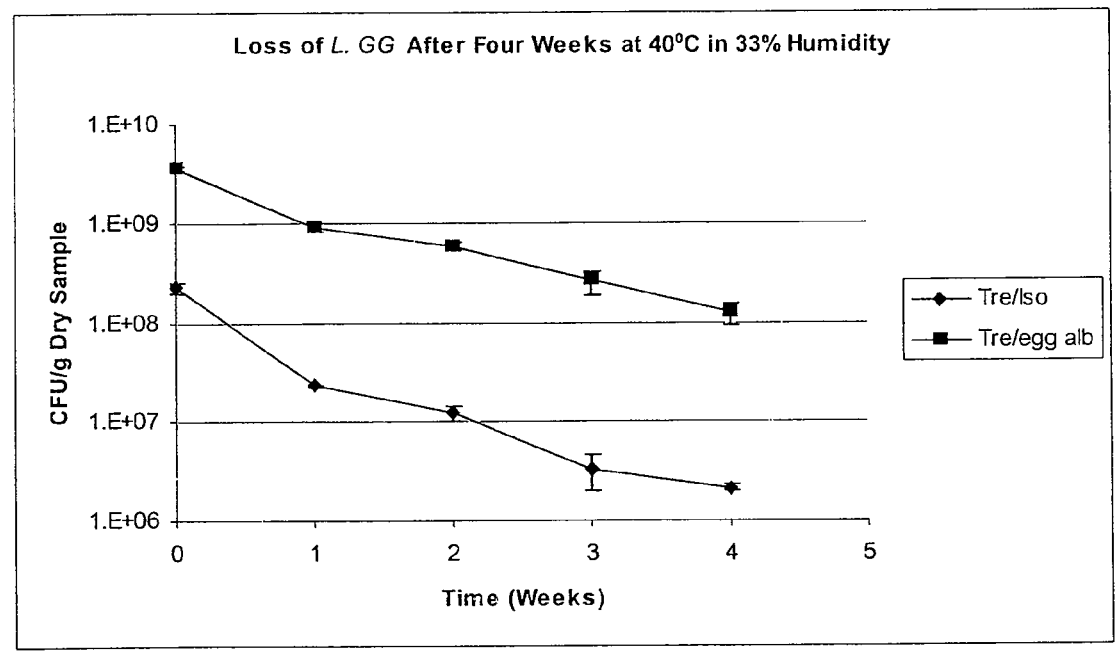

*Lactobacillus* GG was dried as described in example 9. The dried bacteria was placed in temperature and humidity control incubator set at 40° C. and 0% relative humidity, or 40° C. and 33% relative humidity for 4 weeks. Viability of the bacteria was measured every 7 days. FIG. 8 shows that the carbohydrates/polysaccharide/ egg albumen mixture (30% trehalose, 10% egg albumen, 1.5% sodium alginate and 0.5% pectin) provided additional protection to that of trehalose/isomalt alone or free bacteria.

REFERENCES

The following literature references are cited herein.

Bronshtein, V., C. Isaac, And G. Djordjevic. 2004. Preservation Of Bacterial Cells At Ambient Temperatures, EP 1402003.

Chen, T., J. P. Acker, A. Eroglu, S. Cheley, H. Bayley, A. Fowler, and M. Toner. 2001. Beneficial effect of intracellular trehalose on the membrane integrity of dried mammalian cells. *Cryobiology* 43: 168-81.

Crowe, J. H., J. F. Carpenter, and L. M. Crowe. 1998. The role of vitrification in anhydrobiosis. *Annu Rev Physiol* 60: 73-103.

Crowe, L. M., and J. H. Crowe. 1992. Anhydrobiosis: a strategy for survival. *Adv Space Res* 12: 239-47.

Favaro-Trindade, C. S., and C. R. Grosso. 2002. Microencapsulation of *L. acidophilus* (La-05) and *B. lactis* (Bb-12) and evaluation of their survival at the pH values of the stomach and in bile. *J Microencapsul* 19: 485-94.

Franks, F., B. J. Aldous, and A. Auffret. 2003. Stable compositions, U.S. Pat. No. 6,503,411.

Isolauri E, Sutas Y, Kankaanpaa P, Arvilommi H, and S. S. 2001. Probiotics: effects on immunity. Review. *Am J Clin Nutr.* 73: 444S-450S.

Kailasapathy K, and C. J. 2000. Survival and therapeutic potential of probiotic organisms with reference to *Lactobacillus acidophilus* and *Bifidobacterium* spp. Review. *Immunol Cell Biol.* 78: 80-88.

Krallish I, Jeppsson $H_3$ Rapoport A, and H.- H. B. 1997. Effect of xylitol and trehalose on dry resistance of yeasts. *Appl Microbiol Biotechnol.* 47: 447-51.

Liao, Y. H., M. B. Brown, A. Quader, and G. P. Martin. 2002. Protective mechanism of stabilizing excipients against dehydration in the freeze-drying of proteins. *Pharm Res* 19: 1854-61.

Linders L $J_5$ Wolkers W F, Hoekstra F A, and v. t. R. K. 1997. Affect of added carbohydrates on membrane phase behavior and survival of dried *Lactobacillus plantarum. ECryobiology.* 35: 31-40.

Lievense L C, van 't Riet K. 1994. Convective drying of bacteria. II. Factors influencing survival. *Adv Biochem Eng Biotechnol.* 51:71-89.

Marteau P R, de Vrese M, Cellier C J, and S. J. 2001. Protection from gastrointestinal diseases with the use of probiotics. Review. *Am JCHn Nutr.* 73: 430S-436S.

Perdigon G, Fuller R, and R. R. 2001. Lactic acid bacteria and their effect on the immune system. Review. *Curr Issues Intest Microbiol.* 2: 27-42.

Qiu L, Lacey M J, and Bedding R A. 2000. Permeability of the infective juveniles of *Steinernema carpocapsae* to glycerol during osmotic dehydration and its effect on biochemical adaptation and energy metabolism. *Comp Biochem Physiol B Biochem Mol Biol.* 125: 411-9.

Roser, B. J., J. Kampinga, C. Colaco, and J. Blair. 2004. Solid dose delivery vehicle and methods of making same, U.S. Pat. No. 6,811,792.

Shah, N. P. 2000. Probiotic bacteria: selective enumeration and survival in dairy foods. *J Dairy Sd* 83: 894-907.

Simmons, D. L., P. Moslemy, G. D. Paquette, D. Guerin, and M. -H. Joly. 2005. Stable probiotic microsphere compositions and their methods of preparation, PA20050266069.

The disclosure of every patent, patent application, and publication cited herein is hereby incorporated herein by reference in its entirety.

While this subject matter has been disclosed with reference to specific embodiments, it is apparent that, other embodiments and variations can be devised by others skilled in the art without departing from the true spirit and scope of the subject matter described herein. The appended claims include all such embodiments and equivalent variations.

What is claimed is:

1. A method for preparing a preservation mixture, comprising:
   (a) gelling a mixture comprising a polysaccharide, a disaccharide, a sugar alcohol and a probiotic bacterium at a low temperature, whereby a gel mixture is made,
   (b) slicing the gel mixture into small pieces, and
   (c) drying the small pieces under vacuum under conditions suitable for glass formation, whereby the preservation mixture is prepared.

2. The method of claim 1, further comprising cross-linking the polysaccharide in step (a).

3. The method of claim 1, wherein the probiotic bacteria are selected from the group consisting of live *Lactobacillus, Bifidobacterium, Enterococcus, Propionobacterium, Bacillus* and *Streptococcus.*

4. The method of claim 1, wherein the polysaccharide is selected from the group consisting of starch, non-digestible starch, pectin, inulin, xanthan gum, alginate, alginic acid, chitosan, carrageenan, carboxymethyl cellulose, methyl cellulose, guar gum, gum arabic, locust bean gum and combinations thereof.

5. The method of claim 1, wherein the sugar alcohol is selected from the sugar alcohols group consisting of mannitol, sorbitol, xylitol, maltitol, lactitol and isomalt.

6. The method of claim 1, wherein the disaccharide is sucrose.

7. The method of claim 1, further comprising
   (d) maintaining the preservation mixture of step (c) at 40° C.,
   (e) applying to the preservation mixture from step (d) a first vacuum up to 2,500 mTORR for a first period of time; and
   (f) applying to the preservation mixture from step (e) a second vacuum at 100 mTORR for a second period of time.

8. The method of claim 7, wherein the pressure during the first period of time is reduced to 2,500 mTORR.

9. The method of claim 8, wherein the pressure during the second period of time is reduced to less than 100 mTORR.

10. The method of claim 8, wherein the pressure during the first period of time is reduced in increments to the pressure during the second period of time.

11. The method of claim 8, wherein the temperature in the dryer is maintained at 10-20° C. during the first period of time.

12. The method of claim 8, wherein the temperature in the dryer is maintained at 40-50° C. during the second period of time.

13. The method of claim 8, wherein the first period of time lasts from 12 to 16 hours.

14. The method of claim 8, wherein the second period of time stage lasts from 12 to 48 hours.

* * * * *